(12) United States Patent
Tantillo

(10) Patent No.: US 8,569,715 B1
(45) Date of Patent: *Oct. 29, 2013

(54) INFANT STIMULATION AND ENVIRONMENT STERILIZING DEVICE

(71) Applicant: Sylvia Tantillo, Delray Beach, FL (US)

(72) Inventor: Sylvia Tantillo, Delray Beach, FL (US)

(73) Assignee: Jansyl Industries, LLC, Delray Beach, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 13/679,179

(22) Filed: Nov. 16, 2012

Related U.S. Application Data

(63) Continuation-in-part of application No. 12/484,323, filed on Jun. 15, 2009, now abandoned, which is a continuation of application No. 11/784,656, filed on Apr. 9, 2007, now Pat. No. 7,547,893, which is a continuation-in-part of application No. 11/392,014, filed on Mar. 29, 2006, now Pat. No. 7,202,484.

(51) Int. Cl.
*A61L 2/10* (2006.01)

(52) U.S. Cl.
USPC ............ 250/455.11; 250/453.11; 250/454.11; 250/504 R; 250/504 H; 422/20; 422/21; 422/22; 422/24

(58) Field of Classification Search
USPC ............... 250/453.11, 454.11, 455.11, 492.1, 250/493.1, 494.1, 504 R, 504 H; 422/20, 21, 422/22, 24
See application file for complete search history.

(56) References Cited

U.S. PATENT DOCUMENTS

| | | |
|---|---|---|
| 2,592,131 A | 4/1952 | Farrar |
| 3,100,842 A | 8/1963 | Tellefsen |
| 3,711,021 A | 1/1973 | Tantillo |
| 3,967,927 A | 7/1976 | Patterson |
| 4,625,119 A | 11/1986 | Murdock, III |
| 4,806,770 A | 2/1989 | Hylton et al. |
| 4,888,487 A | 12/1989 | Ritter |
| 5,023,460 A | 6/1991 | Foster, Jr. et al. |
| 5,029,252 A | 7/1991 | Ameseder |
| 5,126,572 A | 6/1992 | Chu |
| 5,160,699 A | 11/1992 | Siegal |
| 5,166,528 A | 11/1992 | Le Vay |
| 5,185,532 A | 2/1993 | Zabsky et al. |
| 5,487,877 A | 1/1996 | Choi |
| 6,171,559 B1 | 1/2001 | Sanders et al. |
| 6,461,568 B1 | 10/2002 | Eckhardt |
| 6,558,640 B1 | 5/2003 | Nottingham et al. |
| 6,811,748 B2 | 11/2004 | Ettlinger et al. |
| 7,202,484 B1 * | 4/2007 | Tantillo .................. 250/455.11 |
| 7,547,893 B1 * | 6/2009 | Tantillo .................. 250/455.11 |
| 2004/0106349 A1 | 6/2004 | Green et al. |

(Continued)

*Primary Examiner* — Nicole Ippolito
(74) *Attorney, Agent, or Firm* — Malloy & Malloy, P.L.

(57) ABSTRACT

A cognitive stimulating sterilizing device for providing visual, tactile and, or audible stimulation for infants that also selectively sterilizes select items and the surrounding ambient. This including a housing adapted for removable connection to cribs, changing tables and similar furniture, an ultraviolet light source in the housing for sanitizing items in the housing when closed and the ambient when opened, audio source and compartments for holding and storing select items. The housing may include reflective and/or transparent surfaces for directing and/or passing ultraviolet light. A sensor, such as an infrared sensor, detects the presence of a human in the surrounding area in a motion-independent manner, such as by detecting fluctuations in infrared energy emitted by the human. A microcontroller receives data from the sensor and directs the activation and/or deactivation of the ultraviolet light source according to whether a human is detected.

20 Claims, 11 Drawing Sheets

(56) References Cited

U.S. PATENT DOCUMENTS

| | | | |
|---|---|---|---|
| 2005/0207951 A1* | 9/2005 | Lee et al. | 422/186.07 |
| 2006/0120915 A1 | 6/2006 | Lewandowski | |
| 2006/0281042 A1 | 12/2006 | Rizoiu et al. | |
| 2008/0256741 A1 | 10/2008 | Garcia et al. | |
| 2009/0129974 A1* | 5/2009 | McEllen | 422/24 |

* cited by examiner

INFANT STIMULATION AND ENVIRONMENT STERILIZING DEVICE

CLAIM OF PRIORITY

This application is a continuation-in-part of application Ser. No. 12/484,323 filed on Jun. 15, 2009, which is a continuation of application Ser. No. 11/784,656 filed on Apr. 9, 2007, which issued as U.S. Pat. No. 7,547,893 on Jun. 16, 2009, which is a continuation-in-part of application Ser. No. 11/392,014 filed on Mar. 29, 2006, which issued as U.S. Pat. No. 7,202,484 on Apr. 10, 2007, the contents of all of which are incorporated by reference herein in their entireties.

BACKGROUND OF THE INVENTION

1. Field of the Invention

This invention relates generally to a crib accessory, and more particularly, to a multi-purpose crib accessory that is mountable to an infant's crib or changing table, selectively emits room sterilizing and sanitizing agents into the environment, includes compartments for holding infant care products and provides visual and audible stimulation to promote cognitive development.

2. Description of the Related Art

It is well known that a clean and mentally stimulating environment is important for facilitating health and cognitive development in an infant. An infant's room is often contaminated with airborne bacteria, unhealthy micro-organisms, germs and other unhealthy conditions in the actual dwelling, such as odors, mold, dirt and, or dust, which can adversely affect an infant's health and cognitive development. Sanitizing agents are typically provided in spray cans or bottles, which require the cognizant caretaker to remember to use them. In fact, they may be harmful if used improperly or excessively or by a child. It is also known that infant brains develop and mature when an infant is exposed to visual, audible and tactile stimulation. Colorful and audible mobiles are known in the art but are limited to providing visual and/or audible stimulation. Infant sanitization and brain stimulating products historically comprise separate articles. However, given the dual needs and concerns, it would be beneficial to provide a safe and effective infant stimulation and environment sterilizing device.

Ultraviolet radiation or UVC is reportedly a reliable and safe sterilizing/sanitizing alternative, but has not been effectively adapted for automatically or controllably sterilizing an infant's immediate environment and items. UV-C, also known as germicidal irradiation, lies in the spectrum between 100 and 280 nanometers (nm) and is used for purification of air, water and surfaces. Due to its short wavelength (200 to 270 nm), UV-C penetrates the outer membrane of bacteria, yeasts, molds and viruses, attacking the DNA that makes up their structure. By breaking the chains between the two helixes within the DNA, the microorganism is rendered unable to reproduce, i.e. clinically dead.

Visual and audible mobiles that connect to cribs also exist. However, they fail to offer any environment cleansing benefits or structure for holding infant care products in a conveniently accessible location.

Although various sterilizing products and cognitive development devices are recognized in the prior art, they fail to adequately address or resolve the above noted concerns in a single device for sterilizing the immediate environment while facilitating cognitive growth. The applicant previously obtained U.S. Pat. No. 3,711,021 for a device that suspends from a ceiling and holds hair-grooming articles for use in hair salons, but it fails to address the above noted gap in the prior art. A device that simultaneously and reliably sterilizes an infant's environment while promoting cognitive development, as contemplated by the instant invention, is simply not known. For instance, U.S. Pat. Nos. 2,592,131; 3,100,842; 4,806,770; 4,877,964; 4,888,487; 5,023,460; 5,126,572 and 5,185,532 and U.S. Pat. No. 6,171,559 disclose toothbrush and dental instrument sanitizing devices that merely employ ultraviolet radiation as a sanitation agent. Likewise, U.S. Pat. Nos. 4,625,119; 5,029,252; 5,160,699; 5,166,528; 5,487,877 and 5,979,472 and U.S. Pat. Nos. 6,461,568; 6,558,640 and 6,811,748 only describe devices that utilize ultraviolet light as a sterilizing agent.

As noted, the aforementioned art fails to disclose a device that automatically or controllably employs and emits ultraviolet light to sterilize/sanitize an infant's ambient environment while simultaneously providing visual and audible stimulation for the infant and holding infant care products for conveniently accessible. As the background art fails to disclose a device that adequately addresses these multiple requirements in a single device, there is a need for such a device. The instant invention addresses this need by providing such a device, as contemplated by the instant invention disclosed herein.

SUMMARY OF THE INVENTION

The present invention provides a cognitive stimulating sterilizing device for providing visual, tactile and, or audible stimulation for facilitating cognitive development in infants and toddlers while selectively releasing ultraviolet light to sterilize the surrounding ambient by breaking down airborne bacteria, unhealthy microorganisms, odors and genus and that includes storage compartments for holding health care products, such as wipes, powder and lotions and power receiving or generating devices. The cognitive stimulating sterilizing device comprises a housing adapted for removable mounting to a ceiling, wall or floor stand or removable connection to cribs, changing tables and similar furniture or a stand-alone system; ultraviolet light (UV) generating device in the housing for sanitizing objects placed in the housing and the ambient; microcontroller in electrical communication with the UV light source for automatically energizing or de-energizing the UV light source according to one or more preset times; compartments for holding selected items and incandescent light bulb for providing ambient light. The cognitive stimulating sterilizing device temporarily energizes the UV light source for a predetermined period of time, such as 3-6 minutes, when the housing is closed to sterilize items therein and releases the sterilizing ultraviolet light when the housing is opened to sanitize the ambient. The instant invention includes a microprocessor or timer that controls when power is removed from the UV light source. In the preferred embodiment, the instant invention also includes a mobile projecting from the housing to provide visual stimulation. The housing may include reflective and, or transparent surfaces for directing, reflecting and, or passing ultraviolet light. The instant invention may include visible lights, which may form patterns, using LED's or other light sources, preferably controllable by the microcontroller. The instant invention includes a support frame comprising telescopic tubing for adjusting the height of the housing and that is mountable to a crib, changing table or similar furniture by a clamping device. The tubing may include spaced holes that receive a pin for maintaining a selected elevation.

The housing is preferably spherical, comprising two hemispheres releasably engageable together. The housing includes and, or supports visual, audible and, or tactile stimulating devices removably attached to the housing for replacement with other stimulating devices to vary the stimulation. The housing preferably includes a rotatable section, such as a selected hemisphere or auxiliary ring, for providing a rotatable mobile that may be driven by a motor. The housing may also support at least one sound-generating device having one or more sound generating options to provide audible stimulation. The housing may also provide light stimulation and, or tactile stimulation with three-dimensional objects, which may also be caused to move or vibrate. The timer may be connected to the motor for automatically and, or adjustably removing and connecting power to the motor for rotating the mobile and varying speed of rotation. In accordance with these and other objects, which will become apparent hereinafter, the instant invention will now be described with particular reference to the accompanying drawings.

In at least one embodiment, the system also includes a sensor structured to detect the presence of a human in the surrounding area in a motion-independent manner, such as by infrared (IR), thermal or other electromagnetic or energy emissions. This sensor may be digital, although preferably is analog so as to detect not only emissions, but also fluctuations in those emissions. The sensor is in electrical communication with the microcontroller, such that the UV light source may be activated and/or deactivated based on the readings detected from the sensor. In still other embodiments, the system includes an actuator in mechanical communication with the sensor so as to induce mechanical motion of the sensor or a portion thereof, such as a lens, in order to emulate or induce artificial fluctuations in emissions. Finally, an alarm is present in some embodiments and is structured to emit a warning when a human is detected within an unacceptable distance from an active UV light source.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
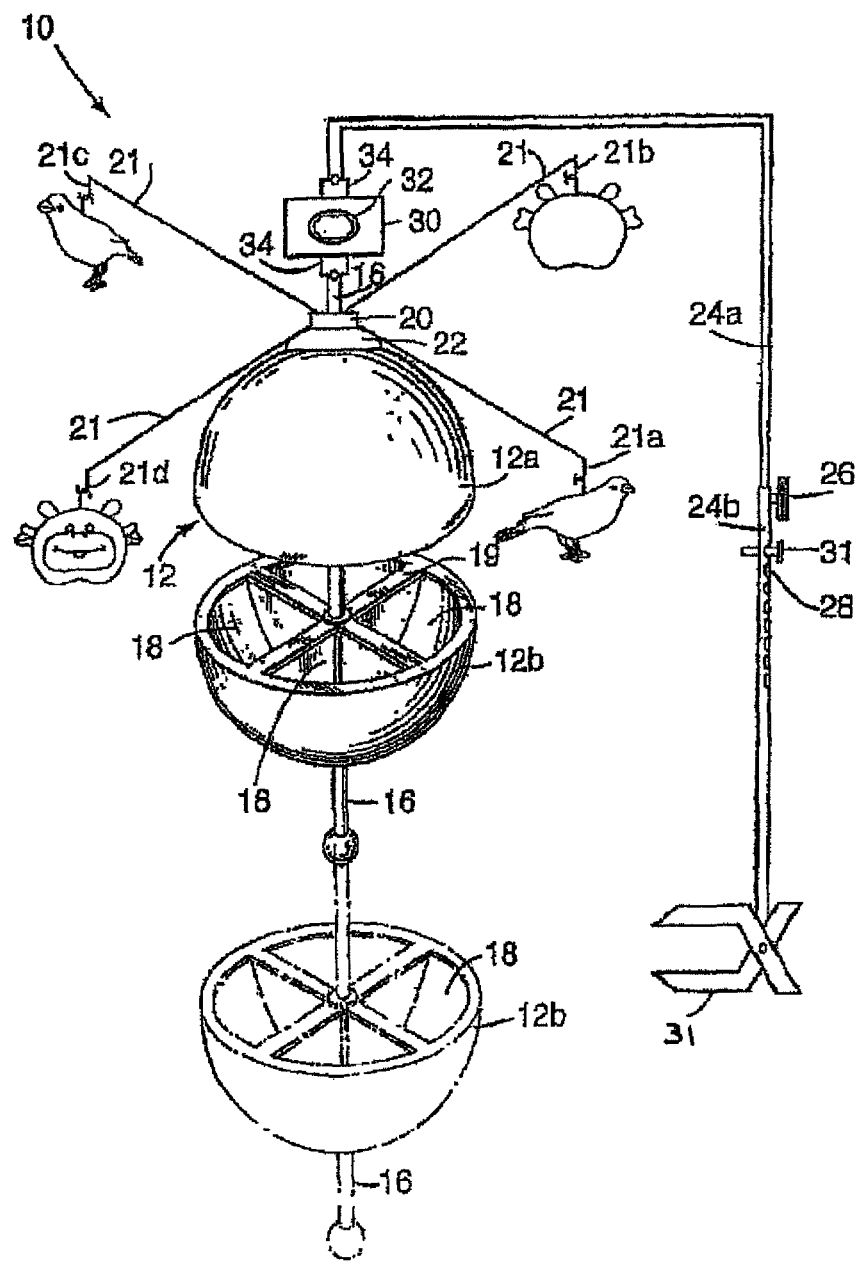
FIG. 1 is a perspective view of one embodiment of the present invention shown in extended and retracted positions.
Figure 2:
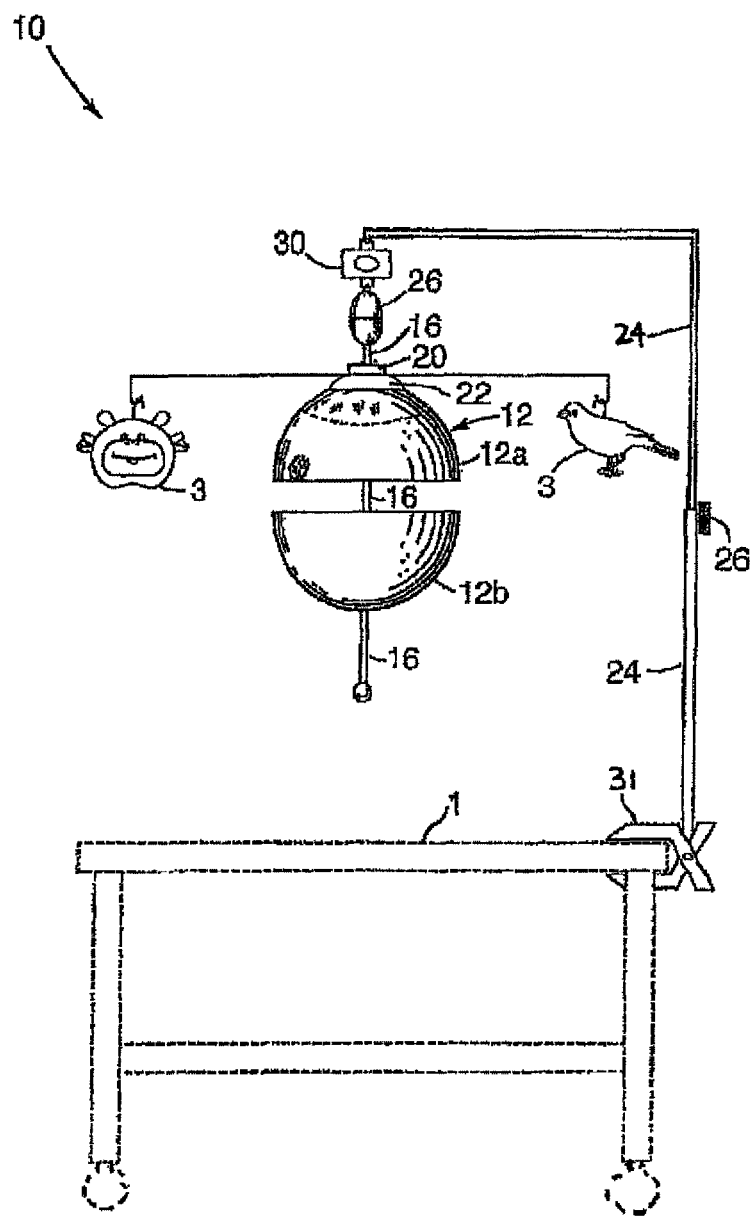
FIG. 2 is an elevational view of another embodiment of the present invention shown in a partially extended position attached to a changing table and having a retraction unit.
Figure 3:
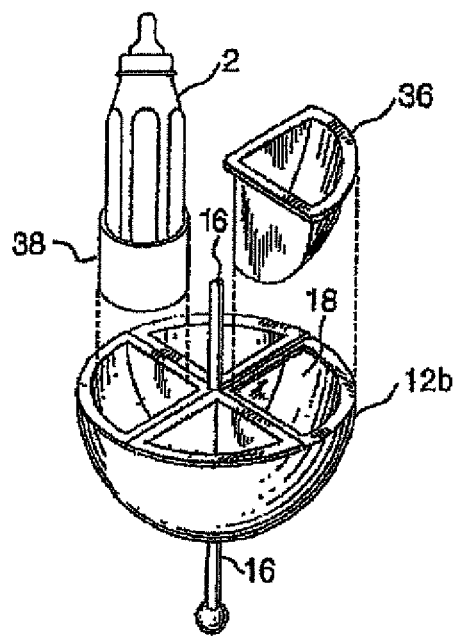
FIG. 3 is a partially exploded view of one embodiment of the instant invention illustrating removable trays and accessories such as bottle warmers.
Figure 4:
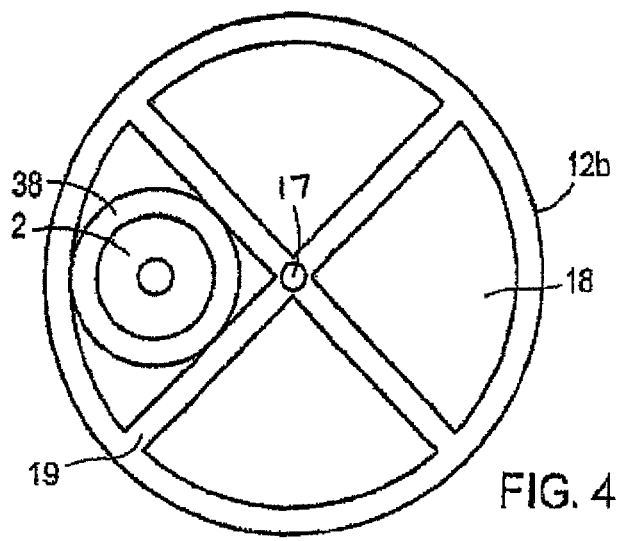
FIG. 4 is a plan view of the lower housing sphere of the instant invention showing the compartments and a bottle in a warmer.
Figure 5:
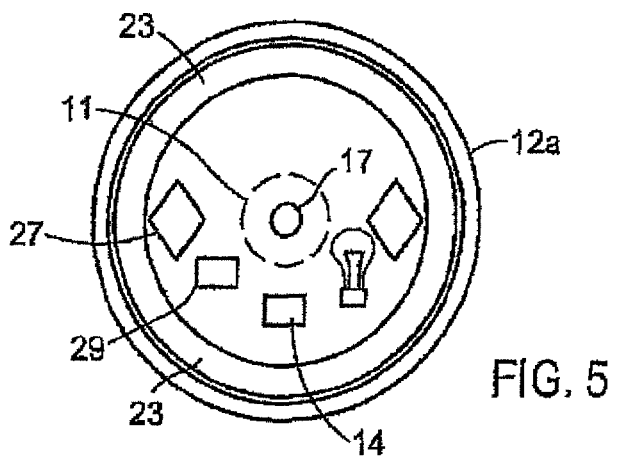
FIG. 5 is a plan view of the upper housing sphere of the instant invention showing the ultraviolet light source.
Figure 6:
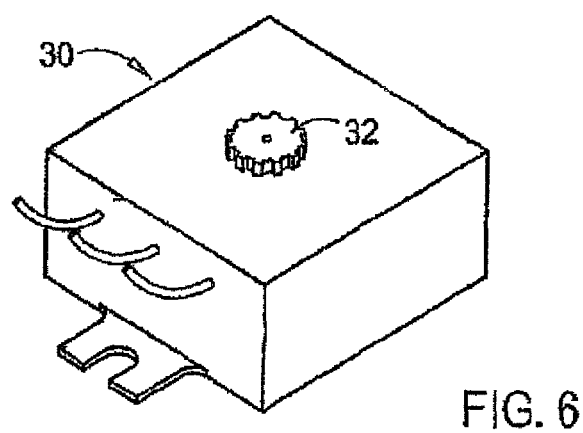
FIG. 6 is a perspective view of the timer of the instant invention.
Figure 7:
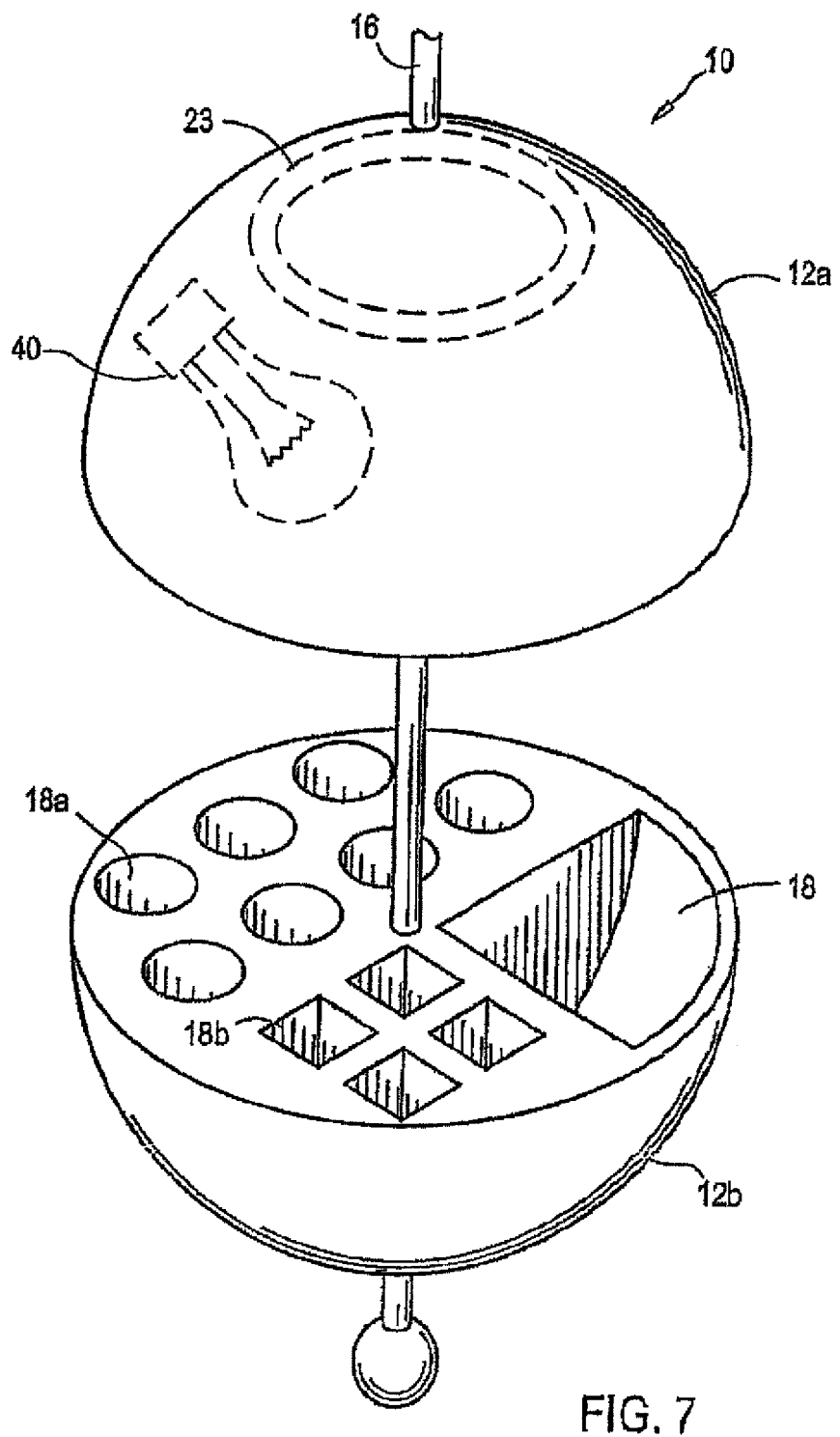
FIG. 7 is a perspective view of an alternative embodiment of the instant invention.
Figure 8:
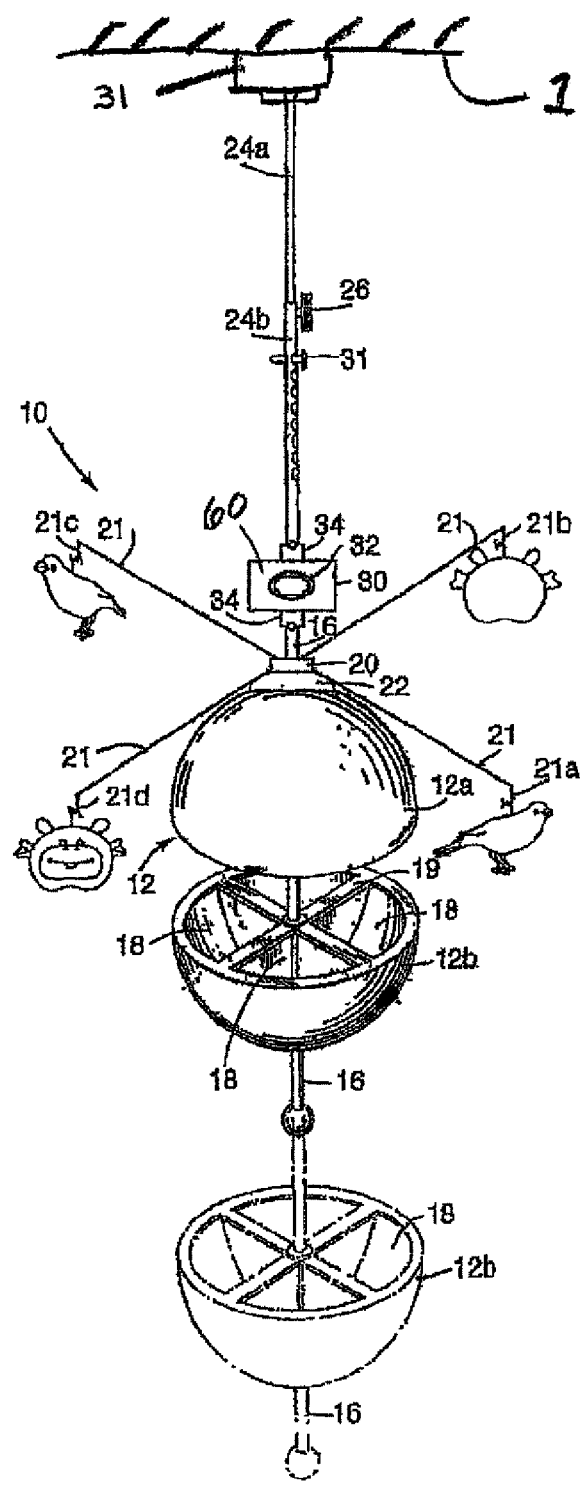
FIG. 8 is a perspective view of an embodiment of the present invention mounted to a ceiling and shown in extended and retracted positions.
Figure 9:
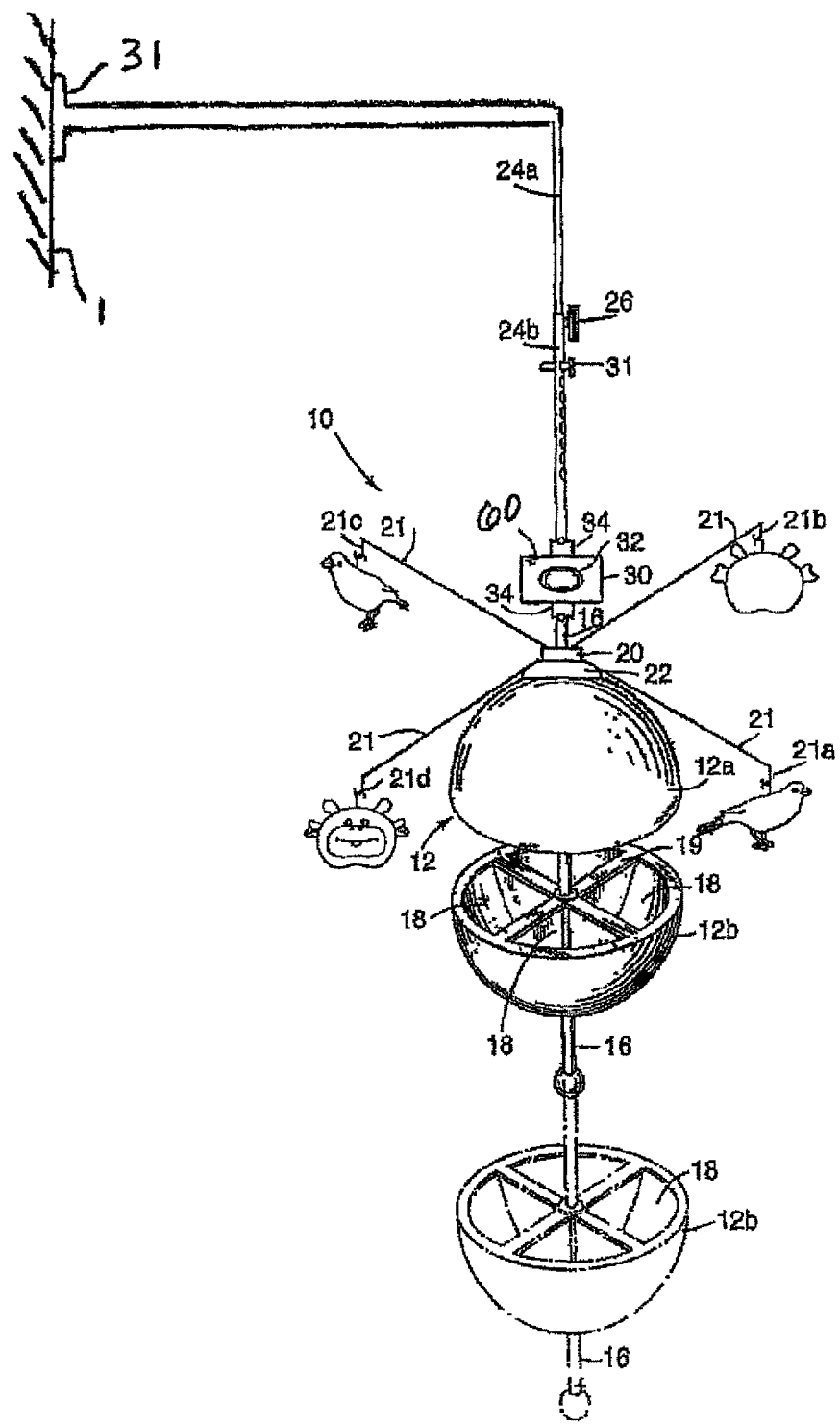
FIG. 9 is a perspective view of another embodiment of the present invention mounted to a wall and shown in extended and retracted positions.
Figure 10:
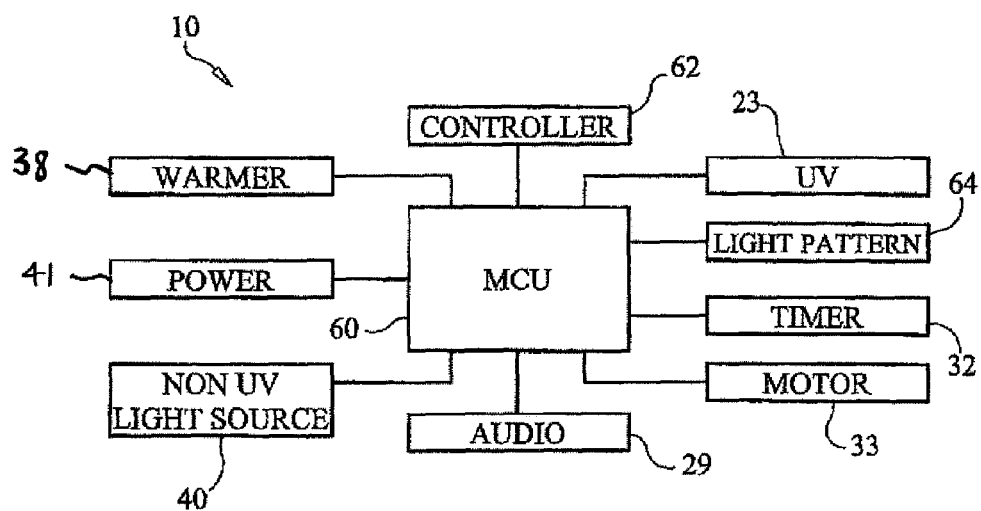
FIG. 10 is an electrical block diagram of one embodiment of the present invention incorporating microcontroller.

With reference to the drawings, FIGS. 1 to 13 depict various embodiments of the instant invention which is generally referenced as an infant cognitive stimulating sterilizing device and, or by numeric character 10. The instant invention is an improvement over the invention disclosed in U.S. Pat. No. 3,711,021, which is incorporated by reference herein, but does not necessarily share the same reference numerals, and has been adapted for an unrelated use. The instant invention 10 comprises a mobile-like device designed for supporting and providing at least one UV light source that attacks and deteriorates airborne organisms, such as bacteria, molds and viruses, releases an air freshener and provides visual and, or audible stimulation to an infant. Power may be received through an internal cord hard-wired to existing power or external cord 42 that plugs into an AC outlet, both of which run through the support rods 24, 16 to 15 drive mechanism 30. Alternatively, the instant invention 10 may be powered by a DC power source, such as batteries. The drive mechanism 30 preferably includes a microprocessor 60 in electrical communication with the ultraviolet (UV) light source 23 for automatically energizing and de-energizing the UV light source 23 according to preset times through an internal or external timer 32, or based on information regarding the presence or lack of presence of a human or other warm-blooded animal in the vicinity, such as provided by a sensor 70. The instant invention 10 may comprise a housing 12 having a variety of geometric shapes, such as a sphere, cube, elliptical, animal or plant.

With reference to FIGS. 1-10, the cognitive stimulating sterilizing device 10 generally comprises a housing 12 having two halves 12a, 12b retractably joinable together along a support rod 16 for opening and closing the housing 12; retractable housing support rod 16 for supporting and facilitating the opening and closing of the housing 12; telescopic mounting rod 24 for supporting and adjusting the height of the housing 12; mounting bracket 32 for mounting the device 10 to a support structure 1 such as a ceiling or wall, crib, changing table, furniture or portable stand having wheels; mobile support rack 21 with hooks 21a-d for removably mounting infant related items designed for facilitating visual stimulation in infants; at least one ultraviolet light source 23 for sterilizing items in the housing 12 and the surrounding area; drive system 30 having a microcontroller 60 with an internal or external timer 32 for automatically applying and removing power to and from the UV light source 23 at one or more preset times; at least one incandescent lamp or light bulb 40 for illuminating the interior of the housing 12 and/or surrounding area when the housing is open; and sound producing device 29 for audible stimulation. The instant invention 10 may also comprise visible entertaining color light source or sources 64, which may provide light patterns, using LED's or other light sources. The audio device 29 may comprise digital music sources such as an mp3 or iPod and USB interfacing. The audio source 29 and entertaining light source(s) 64 are preferably driven by the microcontroller 60, but may be controlled by a separate controller 62. The instant invention 10 may be powered by rechargeable batteries and, or batteries that it can recharge and use. The instant invention 10 may be electrically designed to operate with a wall transformer.

With reference to FIGS. 1-10, the lower housing half 12b comprises a plurality of compartments 18, 18a, 18b for holding items to be stored and sterilized. The shape and number of compartments may vary. The instant invention 10 may include an air freshener 39 that releases a fragrance when the housing 12 is opened. The upper housing half 12a supports and stores the UV light source 23, audio source 29 and light bulb and may also store an air freshener 39, battery compartment 14 and light reflectors 27. The device 10 may include a motor 33 in the drive mechanism 30 for rotating the mobile support rack 21. The housing 12 preferably comprises lightweight molded plastic, although other suitable materials and forming methods could be used.

The UV source 23 comprises at least one UV light bulb 23, such as an ultraviolet germicidal 15-watt to 25-watt hot cathode UV lamp, preferably in the shape of a ring. In the preferred embodiment, power is applied to the ultraviolet light (UV) source 23 when the housing 12 is closed wherein the upper and lower halves 12a, 12b operate as switch 10 or to trigger a switch. The UV light generated by the light source 23 sterilizes items in the housing 12 for a predetermined period of time, such as 2-6 minutes. The timer 32 removes power from the UV light source 23 after the predetermined time period. When the housing 12 is opened, ultraviolet light emanates from the housing 12 to sanitize the surrounding area. The housing 12 may include at least one reflector 27 for directing the UV light. The audio source 29 plays music, stories or other sounds that are comforting, entertaining and, or educational for the infant. The audio source 29 may have its own switch and/or may be activated when the housing is opened or closed. The instant invention 10 preferably includes a timer 32 that removes power from the UV light source after a preset time as adjusted by the operator. The timer 32 may be supported in the drive mechanism 30 and/or in electrical communication with the motor 33 that rotates the mobile 21 for removing power from the motor 33. The timer 32 may be electrically connected to the audio source 29 for removing power from it after a predetermined period of time. A full time cycle could be two minutes to six minutes, or some other selected time. Objects are placed in or near the housing 12 for receiving a direct, concentrated source of sterilizing UV from the UV light source 23.

The cognitive stimulating sterilizing device 10 preferably includes a mobile support rack 21 having hooks 21a-d to interchangeably support animated objects adapted for enjoyment by infants. The number of arms and hooks may vary without departing from the scope and spirit of the instant invention. The mobile support rack 21 may be static but preferably rotates. The motor 33 in the drive system 30 rotates the mobile 21. The instant invention 10 may include a ring 22 rotatably engaged with the upper housing half 12a and electrically connected to the drive system 30 for supporting and rotating the mobile support rack 21, which projects outward there from. Alternatively, the mobile support rack 21 may be connected to the upper or lower housing 12a, 12b. The drive system 30 comprises a motor 33 for turning the ring 22, upper housing 12a and/or lower housing 12b thereby causing the mobile support rack 21 to rotate. The timer 32 may also be used for removing power from the motor after a predetermined period of time. In an alternative embodiment, the invention 10 may include a control circuit for controlling when power is supplied to the motor and/or ultraviolet light source 23.

With reference to the embodiments of FIGS. 1-5 and 7-10, the upper housing half 12a comprises a bowl shape defining an interior volume 13, at least one compartment 18 and support rod aperture 17. The upper housing half 12a may include compartments 18, 18a, 18b having different shapes and sizes. The upper housing 12a supports at least one UV light source 23 and may also support reflectors 27, audio source 29 and air fresheners 39. The upper housing 12a may also include a battery compartment 14 for DC powered versions. A transparent panel 11 may be defined by or incorporated in the upper housing 12a for releasing light from the incandescent lamp 40. Power may be provided to the lamp 40 when the housing 12 is opened or closed or by way of a separate switch. In another embodiment, the transparent panel 11 may be closed to block the passage of light. The support rod 16 passes through the aperture 17 in the upper housing 12. The upper housing 12a is secured to the support rod 16. A slip coupling 20 may mechanically connect the ring 22 to the motor for rotating the ring 22 without rotating the housing 12. Alternatively, the ring 22 may be connected to the upper housing 12a and the coupling to the support rod 16 for rotating the entire assembly.

With reference to FIGS. 1-5 and 7-10, the lower housing 12b preferably comprises a plurality of compartments 18, 18a and/or 18b defined by partitions 19 within its volume for supporting and holding items that need to be sterilized and accessible, such as powder, lotion and/or other infant hygiene items. The lower housing 12b may include a warming device 38, which may be cylindrical or shaped like the compartment 18, for warming bottles and/or wipes. The warmer 38 may be built into the compartment 18 and preferably comprises a heater device as is known in the art. The warmer 38 is electrically connected to the source for receiving power and may comprise a separate switch. The instant invention 10 may comprise removable cups 36 adapted for insertion in the compartments 18, 18a and/or 18b. In at least one embodiment, the removable cups 36 comprise a pair of side walls intersecting at right angles and a third shell-shaped side wall extending from the other ends of sidewalls. The sidewalls terminate at their upper edges in an outwardly extending peripheral flange and are suitably sized so that when the cup 36 is placed in the corresponding conforming compartment 18 the bottom surfaces of the flange sits on the compartment rim. A removable cup 36 enables the user to easily remove the cup for placement on a table or other location where needed.

The housing halves 12a, 12b are secured to the support rod 16. The support rod 16 preferably comprises telescopic tubes that facilitate the opening and closing of the housing 12. The positioning of the lower housing 12b relative to the upper housing 12a is maintained by locking the rod support's 16 tube in a selected position. The support rod 16 may be locked by a twist lock, tabs, spring-loaded buttons for engaging detents or holes or pins for placement in apertures. Alternatively, the rod support 16 may be extended and retracted by a retraction unit 26, such as that described in U.S. Pat. No. 3,711,021. In an alternative embodiment, the lower housing half 12b may slide up and down the rod 16 and interlock with the upper housing half 12a to close the housing 12.

The mounting rod 24 extends from the support rod 16 in a unibody construction or is otherwise mechanically joined to the support rod 16 by the drive system 30 or a known coupling. The mounting rod 24 comprises an adjustable, inverted L-shaped or hook-shaped tube system having a clamp 32 that facilitates attachment to a crib or changing table so the housing attachment end is suspended over the child. The mounting rod 24 comprises an upper mounting rod 24a telescopically joined to a lower mounting rod 24b for slidably adjusting the height of the housing 12. The height of the upper mounting rod 24a may be maintained by retaining screw system 26, spring loaded buttons on one rod with detents or apertures on the other rod, or pin 31 for inserting through apertures on the rods 24a, 24b when aligned. The clamp 32 preferably comprises a spring-loaded clamp that grips furniture when released. Power wires 41 are fed through the mounting rod 24 and support rod 16 for supplying power to the motor 33, timer 32, UV light source 23 and audible source 29.

The drive system 30 comprises the control components of the instant invention 10 and is mounted to the support rod 16 and upper mounting rod 24a. The drive system 30 comprises a motor 33 for rotating the ring 22 and/or support rod 16 and/or timer 32 for removing power from the motor 33, UV light source 23, retraction unit 26 and/or audio source 29. Additional knobs and/or switches may be provided on the drive system 30 for individual control of these components.

In accordance with the foregoing, the instant invention 10 comprises an infant cognitive stimulation sterilizing system, for objects and the ambient environment. The system of the instant invention 10 is mountable in different ways, such as to a ceiling, wall table or mobile cart or base with wheels for portable use in homes or hospitals. The system 10 also comprises lights, which may be incandescent, LED, fiber optic or other known comparable light sources. The system 10 may be loaded with prerecorded audio and/or video or customer recorded audio and/or video files by a USB or wireless link. The system 10 further comprises a USB connector (or other wired or wireless communication links) to enable users to input to the system audio files, video files and/or text or control messages. The system 10 further comprises safety features, such as sensors which detect human presence and pause or stop the UV lights. The system 10 also includes an optional annoying buzzer to further prevent humans from staying within the system proximity when the UV lights are on. It is important to note the housing 12 may comprise various geometric sizes and shapes, such as spherical, cubic, egg-shaped, etc. or any other shape, such as animals, plants, etc.

Figure 11:
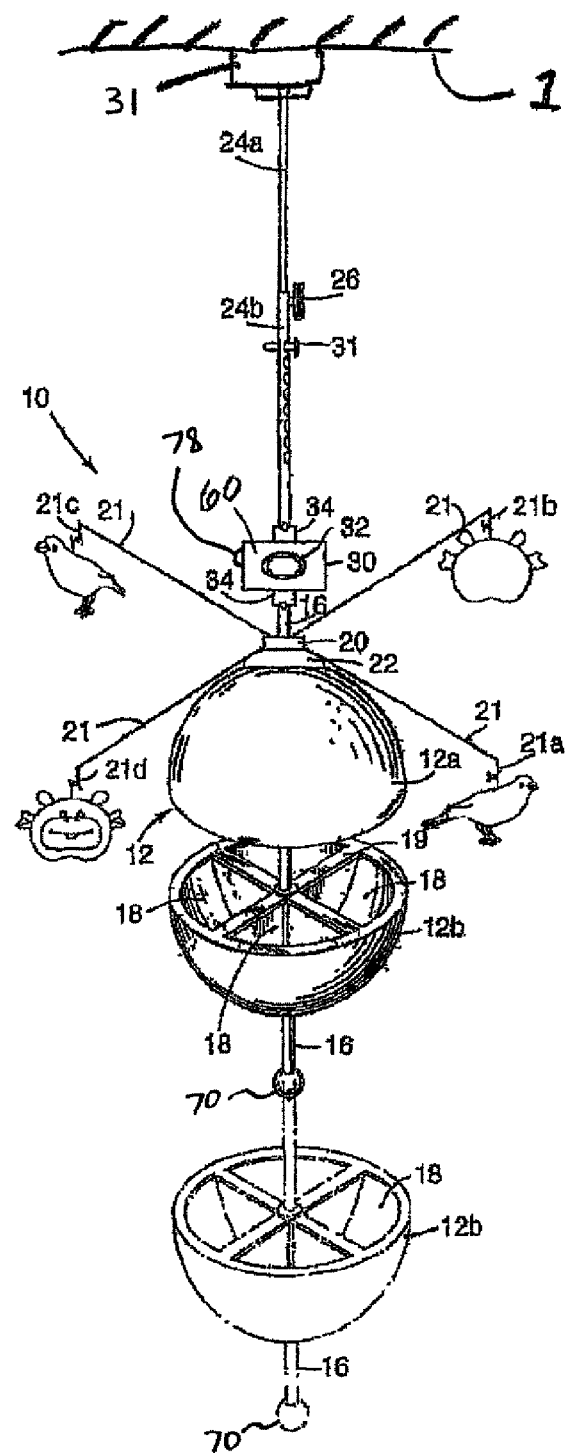
FIG. 11 is a perspective view of one embodiment of the present invention mounted to a ceiling and showing a sensor and alarm.
Figure 12:
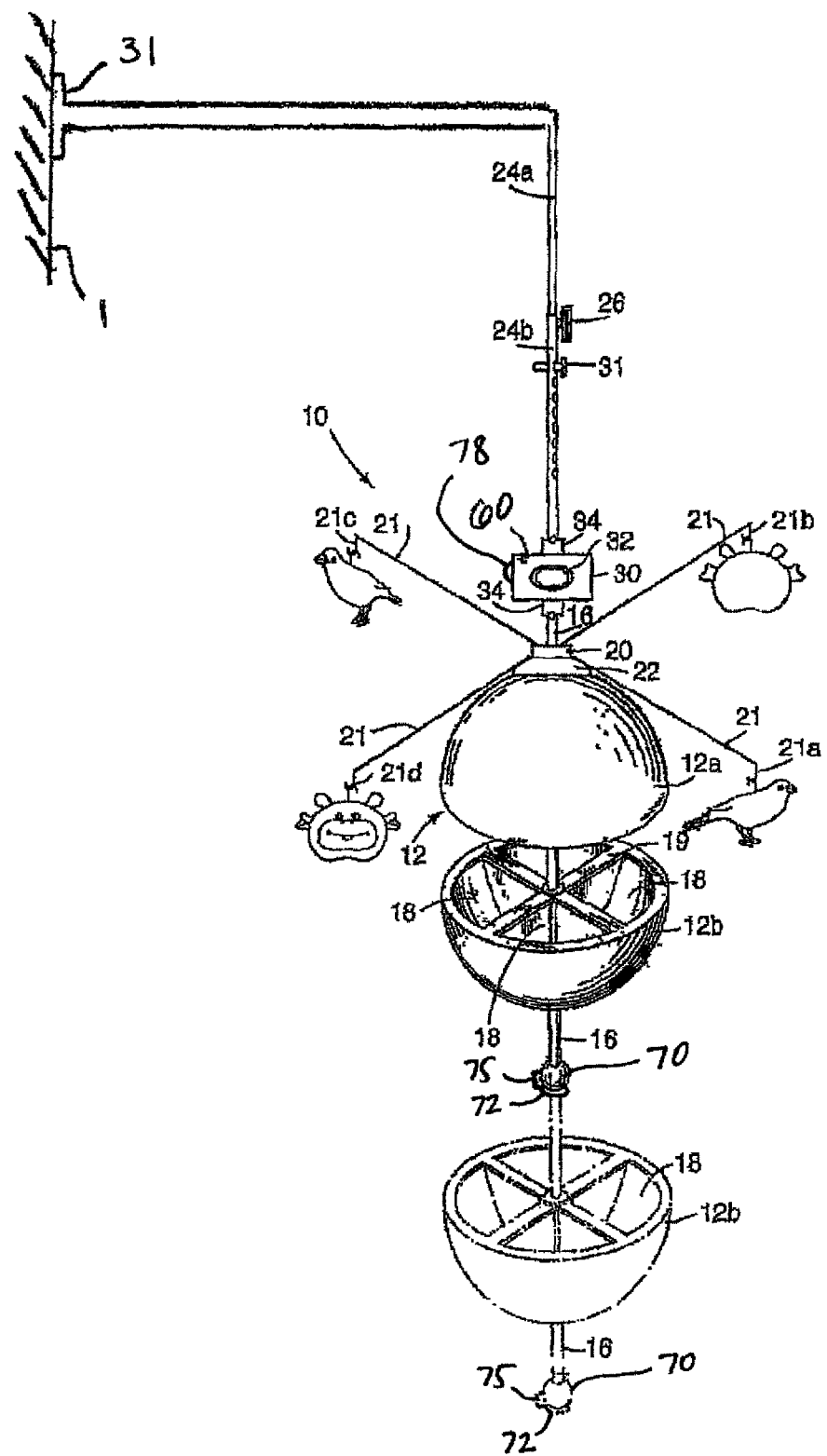
FIG. 12 is a perspective view of another embodiment of the present invention mounted to a wall and showing a sensor and alarm.
Figure 13:
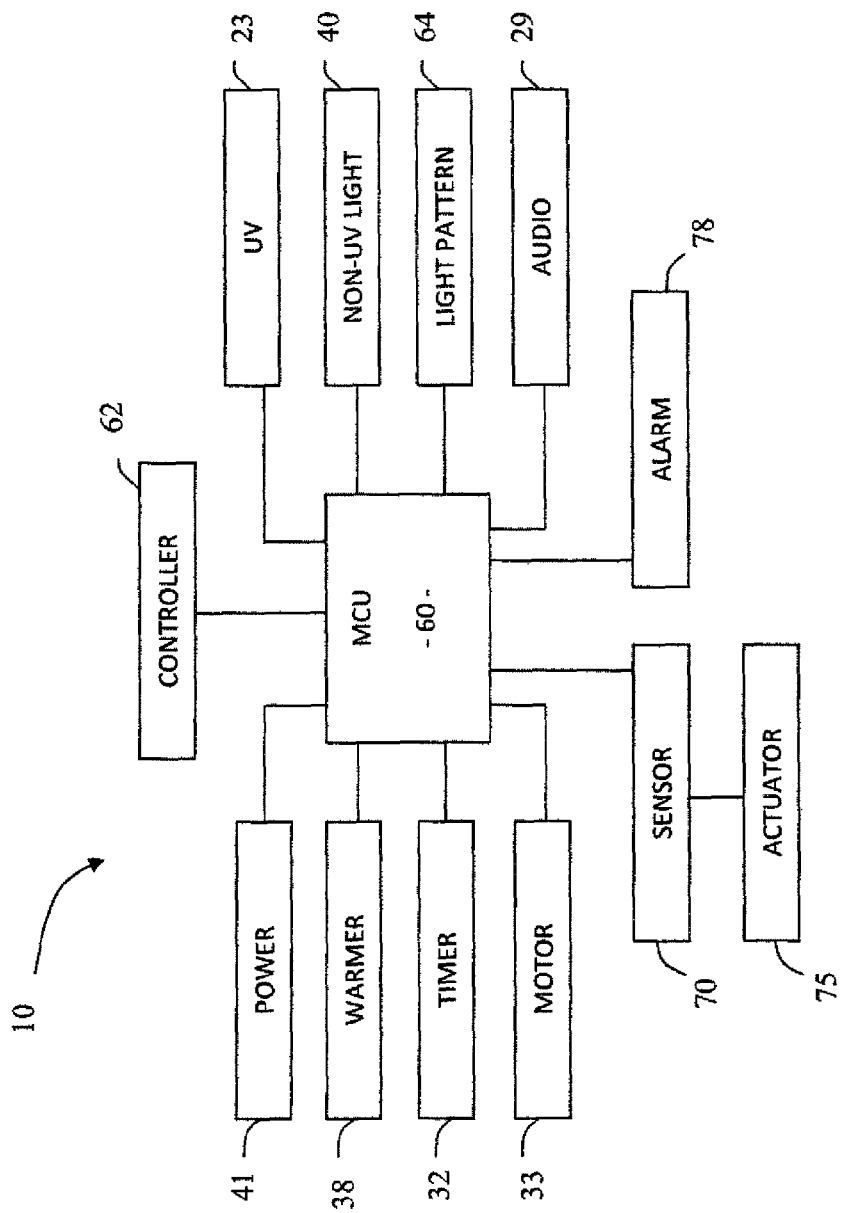
FIG. 13 is an electrical block diagram of one embodiment of the present invention incorporating a sensor.

In another embodiment, as shown in FIGS. 11-13, the infant cognitive stimulation sterilizing system 10 includes a sensor 70 capable of detecting the presence of a human or other warm-blooded animal in the surrounding area. Accordingly, the sensor 70 may be located anywhere on the system 10 which would allow for the detection of a human or other living animal. In one example, the sensor 70 is located on the end of the system 10, such as at the end of the support rod 16 disposed most near to an infant in a crib, in order to effectively detect whether or not an infant is present. For instance, it may be located or suspended a distance of approximately three to four feet above an infant lying in a crib, to be most optimally disposed to detect the presence of an infant. The sensor 70 may be omni-directional so as to also detect whether an adult or other person, such as a parent, sibling, or other person, is within a certain predetermined proximity to the system 10. Of course, it may be located at any other site on the system 10 as would be appropriate to detect the presence of a human, such as on various portions of the housing 12, upper receptacle 12a, lower receptacle 12b, and even support structure 1, etc.

The sensor 70 detects the presence of a human, such as an infant or adult, in a motion-independent manner. Examples include, but are not limited to, infrared or other electromagnetic energy emissions including heat, sound, or other light or energy based methods of detection. For instance, in at least one embodiment the sensor 70 is an infrared (IR) sensor designed to detect infrared energy, and fluctuations in infrared energy, in the surrounding area. More specifically, infrared (IR) light is electromagnetic radiation of wavelengths in the range of approximately 0.74 micrometers to 1,000 micrometers. This range corresponds to energy outside the visible light spectrum, and encompasses the range of thermal emissions from objects near room temperature. Accordingly, IR can be used to detect thermal energy being emitted by objects and living organisms and can therefore be considered a measurement of heat. Moreover, living organisms do not emit a uniform amount of IR or heat, but rather emit varying levels that are constantly changing and fluctuating depending on a number of factors, such as but not limited to movement of the body, changes in body temperature (which can be different on different portions of the body), the impact from the surrounding environment such as a cool breeze on one portion of the body, and even breathing. The sensor 70 of at least one embodiment of the present system 10 detects a human by detecting such changes in IR fluctuation.

This is in contrast to known typical methods of detecting a human which use motion detectors that rely on movement or motion in three-dimensional space to trigger the sensor. The present invention, however, can detect the presence of a human even if that human is not moving. For instance, the sensor 70 can detect fluctuations in IR being emitted by the person. In some embodiments, the sensor 70 is specifically calibrated to detect IR emitted in the surrounding area in a range specifically or particularly emitted by humans or other warm-blooded animals, such as in the range of approximate body temperature, such as generally 98°-103° Fahrenheit. As should already be clear from the discussion above, "IR", "infrared energy", "thermal energy" and "heat" are used interchangeably herein since they are equivalent terms describing the same concept.

The sensor 70 may be any type of sensor capable of detecting the presence of a living creature without relying on motion. In at least one embodiment, the sensor 70 is a chip, and may be implemented within the system 10 on its own or as part of another device. For example, the sensor 70 may include only a chip or other similar structure, which may be discrete or analog as described in greater detail below. In other embodiments, the sensor 70 is a chip or other component of a device, such as a motion sensor. It should be stressed, however, that the sensor 70 does not detect motion, but rather detects the presence of a human in a motion-independent manner, such as via infrared or other electromagnetic energy emissions, including heat, sound, or other light or energy based methods of detection.

As mentioned above, the sensor 70 may be an IR sensor, which can be digital or analog. In the case of a digital sensor, detection is based on a binary system, measuring merely the presence or lack thereof of IR in the surrounding area, such as in a "yes or no" output. In other embodiments, the sensor is analog, which detects not only the presence of energy but also the particular wavelength thereof. The output of an analog sensor is linear and changes higher or lower based on the amount of IR detected over time. Accordingly, analog sensors, such as IR sensors, can quantify and qualify the amount of energy present in a surrounding area.

In one embodiment of the present system 10, the sensor 70 is an analog IR sensor capable of detecting infrared energy levels as quantifiable amounts. The sensor 70 is also therefore capable of detecting fluctuations, or differences over time, of infrared energy as quantifiable amounts since it can detect specific wavelengths and changes in specific wavelengths emitted. The precision of the sensor 70 may vary, but it is contemplated that even very minute changes or fluctuations in IR emission, such as on the order of a tenth of a micrometer in wavelength or less, can be detected.

Moreover, the sensor 70 monitors for energy, such as IR emissions, continuously as long as it is on or engaged. Accordingly, it is capable of detecting fluctuations in energy such as IR over short amounts of time, such as fractions of a second. The sensor 70 may also detect fluctuations in energy as soon as it occurs, as in real-time.

In at least one embodiment, the sensor 70 may lack or specifically not include a lens so as to increase the sensitivity in detecting IR energy. The lack of a lens covering the sensor 70 allows the sensor 70 to more readily accept emissions, such as IR or thermal energy, without being impeded by interference due to motion.

The system 10 further includes a microcontroller 60 disposed in electrical communication with the sensor 70 and with the UV light source 23 so as to receive data from the sensor 70 and provide commands to the UV light source 23. Specifically, when the sensor 70 detects motion-independent emissions, such as IR or thermal energy, the sensor 70 sends or reports this data to the microcontroller 60, which interprets the readings received from the sensor 70. These data may be quantifiable amounts or levels of energy, such as IR, or they may be fluctuations thereof. The microcontroller 60 is programmed to recognize a certain predetermined level of energy, such as IR, to indicate the presence of a human, and any readings falling short of such predetermined level, setting or threshold indicate no human or warm-blooded animal is present. In some embodiments, the predefined settings programmed to indicate human presence are certain wavelengths of light or energy, such as falling within a certain range such as the IR spectrum and may be specifically emitted by humans or other warm-blooded animals. This may also be expressed in heat or thermal readings, such as temperature. Rather than falling within a particular range, in some embodiments a lower level or threshold defines a human presence, such that detection of energy meeting at least that predetermined threshold amount will register as human presence. In other embodiments, the predefined settings are based on fluctuations of readings as opposed to the readings themselves, such as fluctuations of IR wavelengths, and therefore may involve a time component as well. For instance, the microcontroller 60 may be calibrated to a particular threshold level of variation or fluctuation, such that differences in IR levels produced from breathing are sufficient to register and hence detect human presence.

Regardless of how the predefined setting and/or threshold is set, when the microcontroller 60 determines that a human is present in the vicinity, it sends a message or command to the UV light source 23 to turn off, so that humans present in the area are not subjected to UV light. However, if no human presence is detected, the microcontroller 60 sends a command to the UV light source 23 to activate or turn on, so that objects held within the housing 12 and/or the surrounding area can be disinfected with UV light. In at least one embodiment, the microcontroller 60 is structured to automatically activate and/or de-activate the UV light source 23 according to data received from the sensor 70 in view of predefined settings, such as a threshold.

In at least one embodiment, the system 10 further includes an actuator 75 mechanically linked or otherwise in mechanical communication with the sensor 70 so as to selectively activate the sensor 70 upon the occurrence of at least one predetermined event. For instance, the actuator 75 may be used to slightly physically and temporarily move or otherwise mechanically affect the sensor 70 or a portion thereof for a second or other small increment of time, in order to emulate or induce an artificial fluctuation for detection, such as IR in one example. This artificial fluctuation is detected by the sensor 70 and reported to the microcontroller 60.

The actuator 75 may preferably be utilized in certain circumstances, such as when the sensor 70 has not detected any reading in a predetermined amount of time. The actuator 75 can therefore keep the sensor 70 primed and obtaining readings, and can be used to verify that a human is not present in the vicinity. In another example, the actuator 75 can be utilized just before the UV light source 23 is activated or pre-programmed to turn on, so as to check and/or confirm the lack of human presence nearby before commencing disinfection.

The actuator 75 is mechanically coupled to the sensor 70, as noted previously, although it may be located anywhere in the system 10 as is convenient and yet still allow for mechanically affecting the sensor 70. In some embodiments, the actuator 75 is a button, switch, or other similar structure, although not limited to these examples. It may be located on the side of the sensor 70 or on some portion of the housing 12, support rods 16, 24 or drive mechanism 30 that permits mechanical engagement or interconnection with the sensor 70. Moreover, the actuator 75 may be employed manually or automatically, such as on a preprogrammed schedule or predetermined events, examples of which are described previously.

In at least one embodiment, the actuator 75 is structured and in mechanical communication with the sensor 70 so as to induce mechanical motion of a lens 72 associated with or covering at least a portion of the sensor 70. For instance, in embodiments in which the sensor 70 is a component of a larger device, such as detector, a lens 72 may be disposed across the sensor 70 so as to direct incoming IR rays or other type of energy or radiation into the sensor 70 for detection. Mechanically moving the lens 72, even slightly and just for a second, will therefore affect the rays passing therethrough and to the sensor 70, altering the pattern of energy detected, which is measured as fluctuation by the sensor 70. Accordingly, the sensor 70 is artificially activated by the slight motion of the lens 72 as induced by the actuator 75.

In at least one embodiment in which the sensor 70 detects IR or thermal energy, all the heat sources in the room where the system 10 is located, including lights, must be turned off before the actuator 75 is engaged. Since the sensor 70 will detect any objects emitting IR or thermal energy in a particular range, those that emit energy similar to the human body must be removed from the equation before emulating fluctuations so as to avoid false positive readings.

In still another embodiment, the system 10 includes an alarm 78 disposed in electrical communication with the sensor 70. The alarm 78 is structured so as to produce and/or emit a warning when a human is detected within an unacceptable predetermined distance from the UV light source 23. For instance, the alarm 78 may emit a harsh or annoying sound through the audio device 29, which may be very loud, high-pitched, or repetitive. Examples include buzzing, tones, and even spoken recordings that may include instructions to back away. The alarm 78 may also include lights that may flash or alternate, and may be in different colors, so as to swiftly get the attention of any person nearby and alert them to the danger. These lights may include LED or other sources of light.

Moreover, the alarm 78 may be programmed to go off when a human is detected within a certain pre-established proximity to the UV light source 23 when it is activated and UV light is being emitted from the system 10. This distance will depend, at least in part, on the UV light source 23 used, how far its emissions travel, and to what extent the housing 12 is open to allow such UV light to pass into the room. Examples may include a certain number of feet or inches from the UV light source 23. As noted previously, the alarm 78 is electrically coupled to the sensor 70 so that the alarm 78 will be tripped based on certain information as detected by the sensor 70.

The instant invention has been shown and described herein in what is considered to be the most practical and preferred embodiment. It is recognized, however, that departures may be made therefrom within the scope of the invention and that obvious structural and/or functional modifications will occur to a person skilled in the art.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A cognitive stimulating and sterilizing system for holding items and mentally stimulating infants and sanitizing the surrounding area and selected objects, the system comprising:
    a housing having an upper receptacle and lower receptacle;
    a support rod for supporting said housing and facilitating slidable movement of said upper and lower receptacles for opening and closing said housing, said rod comprising at least two rods telescopically joined together;
    an ultraviolet (UV) light source supported in said housing for generating and emanating ultraviolet light at a wavelength calculated to disinfect objects in the surrounding area; and
    a sensor capable of detecting the presence of a human in the surrounding area in a motion-independent manner.

2. The system as recited in claim 1 wherein said sensor is an infrared (IR) sensor capable of detecting infrared energy in the surrounding area.

3. The system as recited in claim 2 wherein said IR sensor is calibrated to detect infrared energy being emitted in the surrounding area in the range specifically emitted by humans.

4. The system as recited in claim 2 wherein said IR sensor is an analog IR sensor capable of detecting infrared energy levels as quantifiable amounts.

5. The system as recited in claim 1 further comprising a microcontroller in electrical communication with said UV light source and said sensor, and structured to automatically activate and de-activate said UV light source according predefined settings to be detected by said sensor.

6. The system as recited in claim 5 wherein said sensor is an analog IR sensor capable of detecting fluctuations of infrared energy as quantifiable amounts.

7. The system as recited in claim 6 wherein said microcontroller directs said UV light source to activate or deactivate based on predetermined threshold levels of infrared energy detected by said sensor.

8. The system as recited in claim 1 further comprising an actuator in mechanical communication with said sensor and structured to induce mechanical motion of a lens of said sensor, thereby selectively activating said sensor, upon the occurrence of at least one predetermined event.

9. The system as recited in claim 1 further comprising an alarm in electrical communication with said sensor and programmed to emit a warning when a human is detected within an unacceptable predetermined distance from said UV light source.

10. A cognitive stimulating and sterilizing system for holding items and mentally stimulating infants and sanitizing the surrounding area and selected objects, the system comprising:
    a housing having an upper receptacle and lower receptacle;
    a support rod for supporting said housing and facilitating slidable movement of said upper and lower receptacles for opening and closing said housing, said rod comprising at least two rods telescopically joined together;
    a mounting rod mechanically communicated with said support rod for adjusting and setting the height that said housing is suspended;
    a mounting member connecting said mounting rod to a selected support structure;
    an ultraviolet (UV) light source supported in said housing for generating and emanating ultraviolet light at a wavelength calculated to disinfect objects in the surrounding area; and
    a sensor capable of detecting the presence of a human in the surrounding area in a motion-independent manner;
    wherein said sensor is an infrared (IR) sensor capable of detecting infrared energy levels in the surrounding area.

11. The system as recited in claim 10 wherein said IR sensor is calibrated to detect infrared energy being emitted in the surrounding area in the range specifically emitted by warm blooded animals.

12. The system as recited in claim 10 wherein said IR sensor includes no lens so as to increase the sensitivity in detecting infrared energy.

13. The system as recited in claim 10 wherein said IR sensor is an analog IR sensor capable of detecting and reporting infrared energy levels as quantifiable amounts.

14. A system as recited in claim 13 further comprising a microcontroller in electrical communication with said UV light source and said IR sensor, and structured to automatically activate and de-activate said UV light source according to predetermined threshold levels of infrared energy as detected by said IR sensor.

15. The system as recited in claim 14 wherein said microcontroller is programmed to direct said UV light source to activate or deactivate based on predefined fluctuations of infrared energy as detected by said IR sensor.

16. The system as recited in claim 10 further comprising an actuator in mechanical communication with said sensor and structured to induce mechanical motion of a lens of said sensor upon the occurrence of at least one predetermined event, thereby selectively activating said sensor.

17. A cognitive stimulating and sterilizing system for holding items and mentally stimulating infants and sanitizing the surrounding area and selected objects, the system comprising:
    a housing having an upper receptacle and lower receptacle;
    a support rod for supporting said housing and facilitating slidable movement of said upper and lower receptacles for opening and closing said housing, said rod comprising at least two rods telescopically joined together;
    a mounting rod mechanically communicated with said support rod for adjusting and setting the height that said housing is suspended;
    a mounting member connecting said mounting rod to a selected support structure;

an ultraviolet (UV) light source supported in said housing for generating and emanating ultraviolet light at a wavelength calculated to disinfect objects in the surrounding area;

an infrared (IR) sensor capable of detecting infrared energy in the surrounding area; and a microcontroller in electrical communication with said UV light source and said IR sensor for automatically activating and de-activating said UV light source according to levels or fluctuations in infrared energy detected by said IR sensor.

18. The system as recited in claim 17 wherein said IR sensor includes no lens so as to increase the sensitivity in detecting infrared energy.

19. The system as recited in claim 17 wherein said IR sensor is an analog IR sensor capable of detecting quantifiable amounts of infrared energy levels and fluctuations in infrared energy levels.

20. The system as recited in claim 17 further comprising an actuator in mechanical communication with said sensor and structured to induce mechanical motion of a lens of said sensor upon the occurrence of at least one predetermined event, thereby selectively activating said sensor.

* * * * *